United States Patent
Lan et al.

(10) Patent No.: US 11,795,370 B2
(45) Date of Patent: Oct. 24, 2023

(54) ANTI-AGGLOMERANT HYDRATE INHIBITORS AND METHOD OF USE

(71) Applicant: Multi-Chem Group, LLC, San Angelo, TX (US)

(72) Inventors: Qiang Lan, The Woodlands, TX (US); Deepak S. Monteiro, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 320 days.

(21) Appl. No.: 17/270,589

(22) PCT Filed: Sep. 25, 2018

(86) PCT No.: PCT/US2018/052522
§ 371 (c)(1),
(2) Date: Feb. 23, 2021

(87) PCT Pub. No.: WO2020/068046
PCT Pub. Date: Apr. 2, 2020

(65) Prior Publication Data
US 2021/0253937 A1    Aug. 19, 2021

(51) Int. Cl.
*C09K 8/52* (2006.01)
*C07C 211/63* (2006.01)
*E21B 43/16* (2006.01)

(52) U.S. Cl.
CPC .............. *C09K 8/52* (2013.01); *C07C 211/63* (2013.01); *E21B 43/16* (2013.01); *C09K 2208/22* (2013.01)

(58) Field of Classification Search
CPC ...... C09K 8/52; C09K 2208/22; C09K 8/035; C07C 211/63; E21B 43/16; C10L 3/107
See application file for complete search history.

(56) References Cited

U.S. PATENT DOCUMENTS

| | | | |
|---|---|---|---|
| 2,976,307 A * | 3/1961 | Rudner | C07F 5/003 556/172 |
| 4,873,370 A | 10/1989 | Chiu | |
| 5,648,575 A | 7/1997 | Klomp et al. | |
| 7,183,240 B2 | 2/2007 | Dahlmann et al. | |
| 7,381,689 B2 | 6/2008 | Panchalingham et al. | |
| 8,134,011 B2 | 3/2012 | Rivers et al. | |
| 8,329,620 B2 | 12/2012 | Acosta | |
| 8,404,895 B2 | 3/2013 | Tian et al. | |
| 8,618,025 B2 | 12/2013 | Webber | |
| 2006/0094623 A1 * | 5/2006 | Erkenbrecher, Jr. | C11D 3/2082 510/301 |
| 2018/0010036 A1 | 1/2018 | Qu et al. | |
| 2018/0155607 A1 | 6/2018 | Lan et al. | |

FOREIGN PATENT DOCUMENTS

| | | | | |
|---|---|---|---|---|
| WO | 2016/105338 A1 | 6/2016 | | |
| WO | 2017/105507 A1 | 6/2017 | | |
| WO | WO-2017105507 A1 * | 6/2017 | ........... | C07C 233/36 |
| WO | 2018115186 A1 | 6/2018 | | |

OTHER PUBLICATIONS

International Search Report and Written Opinion issued in related PCT Application No. PCT/US2018/052522 dated Jun. 19, 2019, 12 pages.
Szönyi, S., H. J. Watzke, and A. Cambon. "Highly fluorinated surfactants in liposome technology." Thin solid films 284 (1996): 769-771.
Foreign Communication from Related Application—Netherlands Search Report, NL Application No. 2023658, dated Oct. 28, 2022, 7 pages.

* cited by examiner

*Primary Examiner* — Kumar R Bhushan
(74) *Attorney, Agent, or Firm* — Conley Rose, P.C.; Rodney B. Carroll

(57) ABSTRACT

Compositions and methods of using such compositions to inhibit the formation of gas hydrate agglomerates are provided. In certain embodiments, the methods include: contacting a fluid with a hydrate inhibitor composition that includes at least one compound having the structural formula (I) wherein $R_1$ is hydrogen or any $C_1$ to $C_8$ hydrocarbon chain; each of $R_2$ and $R_3$ is independently a $C_1$ to $C_8$ hydrocarbon chain; $R_4$ is hydrogen, a $C_1$ to $C_{20}$ hydrocarbon chain, or —$CH_2$—$CH(OH)$—$R_5$; $R_5$ is a $C_1$ to $C_{50}$ alkyl chain or a $C_1$ to $C_{50}$ alkenyl chain; $X^-$ is a counter anion; and n is an integer from 1 to 8.

20 Claims, 1 Drawing Sheet

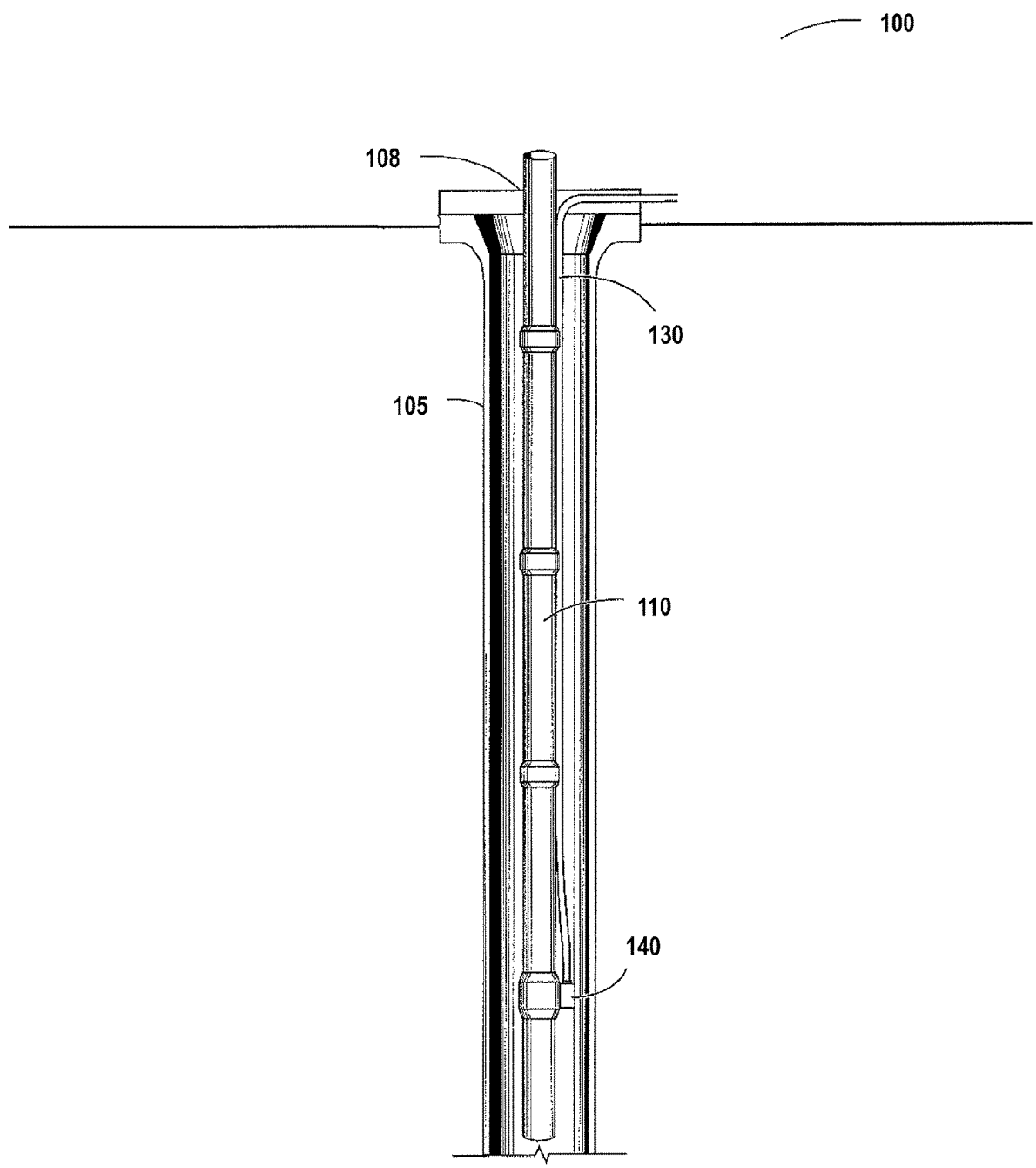

ANTI-AGGLOMERANT HYDRATE INHIBITORS AND METHOD OF USE

CROSS-REFERENCE TO RELATED APPLICATION

The present application is a U.S. National Stage Application of International Application No. PCT/US2018/052522 filed Sep. 25, 2018, which is incorporated herein by reference in its entirety for all purposes.

BACKGROUND

The present disclosure relates to compositions and methods useful in processes involving fluid flowing through, or contained in, wellbores penetrating subterranean formations or conduits, such as pipes used, e.g., for the production and/or transport of petroleum products, natural gas, and the like.

Gas hydrates are typically solids that may agglomerate in a fluid that is flowing or is substantially stationary, under certain temperature and pressure conditions. For example, gas hydrates may form during hydrocarbon production from a subterranean formation, in pipelines and other equipment during production operations. Hydrates may impede or completely block flow of hydrocarbons or other fluid flowing through such pipelines. These blockages not only may decrease or stop production, potentially costing millions of dollars in lost production, but also may be very difficult and dangerous to mediate. Unless properly handled, gas hydrates may be volatile and even explosive, potentially rupturing pipelines, damaging equipment, endangering workers, and causing environmental harm.

Gas hydrates may form when water molecules become bonded together after coming into contact with certain "guest" gas or liquid molecules. Hydrogen bonding may cause the water molecules to form a regular lattice structure, like a cage, that is stabilized by the guest gas or liquid molecules entrapped within the lattice structure. The resulting crystalline structure may precipitate as a solid gas hydrate. Guest molecules can include any number of molecules such as, for example, carbon dioxide, methane, butane, propane, hydrogen, helium, freon, halogen, noble gases, and the like.

BRIEF DESCRIPTION OF THE DRAWING

This drawing illustrates certain aspects of some of the embodiments of the present disclosure and should not be used to limit or define the claims.

FIG. 1 is a diagram illustrating an injection system used in accordance with certain embodiments of the present disclosure.

While embodiments of this disclosure have been depicted, such embodiments do not imply a limitation on the disclosure, and no such limitation should be inferred. The subject matter disclosed is capable of considerable modification, alteration, and equivalents in form and function, as will occur to those skilled in the pertinent art and having the benefit of this disclosure. The depicted and described embodiments of this disclosure are examples only, and not exhaustive of the scope of the disclosure.

DESCRIPTION OF CERTAIN EMBODIMENTS

Illustrative embodiments of the present disclosure are described in detail herein. In the interest of clarity, not all features of an actual implementation may be described in this specification. It will of course be appreciated that in the development of any such actual embodiment, numerous implementation-specific decisions may be made to achieve the specific implementation goals, which may vary from one implementation to another. Moreover, it will be appreciated that such a development effort might be complex and time-consuming, but would nevertheless be a routine undertaking for those of ordinary skill in the art having the benefit of the present disclosure.

To facilitate a better understanding of the present disclosure, the following examples of certain embodiments are given. In no way should the following examples be read to limit, or define, the scope of the invention. Embodiments of the present disclosure involving wellbores may be applicable to horizontal, vertical, deviated, or otherwise nonlinear wellbores in any type of subterranean formation. Embodiments may be applicable to injection wells, monitoring wells, and production wells, including hydrocarbon or geothermal wells.

The present disclosure relates to compositions and methods useful in processes involving fluid flowing through, or contained in, wellbores penetrating subterranean formations or conduits, such as pipes used, e.g., for the production and/or transport of petroleum products, natural gas, and the like. More particularly, the present disclosure relates to compositions and method of using such compositions to, for example, inhibit the formation of gas hydrate agglomerates.

In certain embodiments, the present disclosure may provide certain hydrate inhibitor compounds (e.g., low dosage hydrate inhibitors or "LDHI"s) having the following formula:

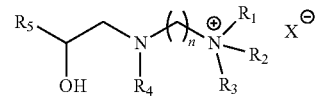

In some embodiments, the R groups and other variables in the formula above may be as follows. $R_1$ may be selected from the group consisting of hydrogen and any $C_1$ to $C_8$ hydrocarbon chain. $R_2$ and $R_3$ may independently be any $C_1$ to $C_8$ hydrocarbon chain. $R_4$ may be selected from the group consisting of hydrogen, any $C_1$ to $C_{20}$ hydrocarbon chain, and —$CH_2$—$CH(OH)$—$R_5$. $R_5$ may be a $C_1$ to $C_{50}$ alkyl or alkenyl group. $X^-$ may be a counter anion, and n may be an integer from 1 to 8.

In certain embodiments, the hydrate inhibitors of the present disclosure may include a lipophilic tail, a hydrophilic head, and a linking moiety. In some embodiments, the hydrate inhibitor compounds may be provided, used, and/or introduced as a salt. In certain embodiments, the present disclosure further provides methods of using such hydrate inhibitor compounds to inhibit the formation of one or more hydrates in a fluid. For example, certain embodiments of the present disclosure provide methods of adding a composition including one or more hydrate inhibitor compounds of the present disclosure to a fluid which may include any one or more of water, a gas, a liquid hydrocarbon, and any combination thereof. In certain embodiments, such a method may include adding to the fluid an effective amount of a hydrate inhibitor compound of the present disclosure to inhibit, retard, reduce, control, delay, and/or the like the formation of hydrate agglomerates.

Among the many advantages to the compositions and methods of the present disclosure, only some of which are alluded to herein, the hydrate inhibitor compounds and methods of the present disclosure may, among other benefits, provide for enhanced anti-agglomeration properties and/or enhanced inhibition, retardation, mitigation, reduction, control, delay, and/or the like of agglomeration of hydrates and/or hydrate-forming compounds. In certain embodiments, agglomeration of hydrates and/or hydrate-forming compounds (and the like) may be reduced and/or inhibited to a greater degree than that achieved using other hydrate inhibition means. In particular embodiments, compounds of the present disclosure may provide enhanced inhibition of agglomeration of hydrates and/or hydrate-forming compounds. In some embodiments, the hydrate inhibitor compounds of the present disclosure may be substantially or entirely free of organic halides, which may be required and/or desirable relative to certain environmental, safety-related, and/or other operational requirements.

The hydrate inhibitor compounds of the present disclosure may include a hydrophilic head that includes a cation moiety, which may be a quaternary ammonium cation moiety or a tertiary ammonium cation moiety. In certain embodiments, the cation moiety in the hydrate inhibitor compounds of the present disclosure may be bonded to other moieties of the hydrate inhibitor compound. In certain embodiments, the cation moiety may be substantially of the composition $-R_1R_2R_3N^+$, and may correspond to the corresponding portion of the structural formula shown above. In that formula, $R_1$ may be selected from the group consisting of a hydrogen atom or a $C_1$ to $C_8$ hydrocarbon chain, and each of the $R_2$ and $R_3$ may independently include either a hydrogen atom or any $C_1$ to $C_8$ hydrocarbon chain. As used herein, a "hydrocarbon chain" may, unless otherwise specifically noted, be branched, unbranched, non-cyclic, and/or cyclic; it may be substituted or unsubstituted (that is, it may or may not contain one or more additional moieties or functional groups in place of one or more hydrogen atoms in the hydrocarbon chain); and/or it may be saturated or unsaturated. Furthermore, as used herein, the nomenclature "$C_x$ to $C_y$," refers to the number of carbon atoms in the hydrocarbon chain (here, ranging from x to y carbon atoms). As used herein, "independently" refers to the notion that the preceding items may be the same or different.

In certain embodiments, $R_1$ may be a hydrogen atom. In other embodiments, each of $R_1$, $R_2$, and $R_3$ may independently include a $C_1$ to $C_8$ hydrocarbon chain. In such embodiments wherein at least one of $R_1$, $R_2$, and/or $R_3$ includes a $C_1$ to $C_8$ hydrocarbon chain, the hydrocarbon chain may include any one or more hydrocarbon groups selected from the group consisting of: alkyl, alkenyl, alkynyl, aryl, arylalkyl, arylalkenyl, alkylaryl, alkenylaryl, and any combination thereof. In such embodiments, any one or more of $R_1$, $R_2$, and $R_3$ may be branched, unbranched, non-cyclic, cyclic, saturated, and/or unsaturated. In certain embodiments, each of $R_1$, $R_2$, and $R_3$ may independently include (i) as few as any one of: 1, 2, 3, 4, 5, 6, 7, and 8 carbon atoms, and (ii) as many as one of: 2, 3, 4, 5, 6, 7, and 8 carbon atoms. For example, suitable ranges of carbon atoms in each of $R_1$, $R_2$, and $R_3$ according to various embodiments of the present disclosure include, but are not limited to, 1 to 2, 1 to 3, 1 to 4, 1 to 5, 1 to 6, 1 to 7, 1 to 8, 2 to 4, 3 to 5, 4 to 6, 5 to 7, 6 to 8, and the like.

In some embodiments, any one or more of $R_1$, $R_2$, and $R_3$ may include a $C_1$ to $C_8$ alkyl chain. In some embodiments, any one or more of $R_1$, $R_2$, and $R_3$ may include a $C_2$ to $C_8$ alkenyl or alkynyl chain. In some embodiments, any one or more of $R_1$, $R_2$, and $R_3$ may include a $C_3$ to $C_8$ cyclic moiety. In certain embodiments, any one or more of $R_1$, $R_2$, and $R_3$ may be substituted (e.g., it may include any one or more functional groups in addition to the hydrocarbon groups described above), so long as the cation moiety remains hydrophilic.

The hydrate inhibitor compounds of the present disclosure may include a lipophilic tail, e.g., shown as $R_5$ in the structural formula shown above. In certain embodiments, the lipophilic tail of the hydrate inhibitor compounds of the present disclosure may each independently be selected from the group consisting of a $C_1$ to $C_{50}$ long alkyl or alkenyl group. In certain embodiments, the alkyl or alkenyl group of the lipophilic tail may be branched or unbranched, cyclic or non-cyclic, and/or saturated or saturated, and/or may contain any one or more hetero-atoms (e.g., oxygen, nitrogen, sulfur, etc.), and/or any combination thereof. In certain embodiments, the lipophilic tail may further optionally be substituted with any one or more functional groups, so long as such substituted functional group(s) do not alter the lipophilic and/or hydrophobic nature of the lipophilic tail. In certain embodiments, each of the lipophilic tails may independently include (i) as few as any one of: 1, 2, 3, 4, 5, 6, 7, 8, 9, 10, 11, 12, 13, 14, 15, 16, 17, 18, 19, and 20 carbon atoms, and (ii) as many as any one of: 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, and 50 carbon atoms. For example, suitable ranges of carbon atoms in the lipophilic tail according to various embodiments of the present disclosure may include, but are not limited to, 1 to 5, 3 to 5, 4 to 8, 5 to 15, 8 to 18, 12 to 16, 8 to 20, 10 to 20, 15 to 20, and the like. It will be appreciated by one of ordinary skill in the art having the benefit of the present disclosure that even in such embodiments, additional lipophilic tails may be included in the hydrate inhibitor compound (e.g., at locations other than the $R_5$ group in the structural formula shown above).

The hydrate inhibitor compounds of the present disclosure may include a linking moiety. As used herein, "linking moiety" refers to any portion of the hydrate inhibitor compound between the hydrophilic head and the lipophilic tail. In certain embodiments, the lipophilic tail may be connected to the hydrophilic head via the linking moiety. For example, lipophilic tail $R_5$ may be connected to the hydrophilic head $R_1R_2R_3N^+$ via the linking moiety $-CH_2-CH(OH)-N(R_4)-C_nH_{2n}-$. In certain embodiments, the linking moiety may provide sufficient spacing between the hydrophilic head and the lipophilic tail so that the hydrate inhibitor compound maintains an overall substantially amphiphilic character.

The linking moiety of the hydrate inhibitor compound may include an amine functional group. In such embodiments, the amine functional group that may be included on the linking moiety should not adversely affect the hydrophilic nature of a hydrophilic head, nor should it adversely affect the lipophilic nature of the lipophilic tail. The amine functional group may be a secondary amine or a tertiary amine. In certain embodiments where the linking moiety includes a secondary amine, $R_4$ in the structural formula shown above may be a hydrogen atom. In certain embodiments where the linking moiety includes a tertiary amine, $R_4$ may be a $C_1$ to $C_{20}$ hydrocarbon chain, or $-CH_2-CH(OH)-R_5$.

In certain embodiments, the linking moiety includes an amine functional group including two alkyl chains on either side connecting the lipophilic tail to the hydrophilic head. The alkyl chain of the linking moiety connecting the lipophilic tail may include a hydroxyl group and have the general formula $-CH_2-CH(OH)-$. The alkyl chain of the linking moiety connecting the hydrophilic head may have the general formula $C_nH_2n$, wherein n may be an integer from 1 to 8. In certain embodiments, the alkyl chain of the linking moiety connecting the hydrophilic head may include (i) as few as any one of: 1, 2, 3, 4, 5, 6, 7, and 8 carbon atoms, and (ii) as many as any one of: 2, 3, 4, 5, 6, 7, and 8 carbon atoms.

The hydrate inhibitor compounds of the present disclosure may instead or in addition be characterized as reaction products. The raw materials used for preparing the disclosed hydrate inhibitor compounds may be commercially available. For instance, in some embodiments, the present disclosure provides hydrate inhibitor compounds that may be characterized as reaction products of: (1) a dialkylaminoalkylamine and (2) a 1,2-epoxyalkane. In some embodiments, the "dialkyl" groups of the dialkylaminoalkylamine may be either the same or different, and $R_2$ and $R_3$ of the cation moiety may depend upon, among other factors, the identity of the dialkyl groups of the dialkylaminoalkylamine.

In some embodiments, the reaction product of (1) the dialkylaminoalkylamine and (2) the 1,2-epoxyalkane may form a first intermediate that may further be reacted with one or more alkylating agents. In such embodiments, $R_1$ of the cation moiety may depend upon, among other factors, the alkyl group of the alkylating agent(s). In certain embodiments, the one or more alkylating agents may be an alkyl halide, diethyl sulfate, dimethyl carbonate, and/or any combination thereof. In other embodiments where the $R_1$ of the cation moiety is a hydrogen atom, the reaction product of (1) the dialkylaminoalkylamine and (2) the 1,2-epoxyalkane may form a first intermediate that may further be reacted with one or more acids.

In certain embodiments, the hydrate inhibitor compounds of the present disclosure may be provided, used, and/or introduced as a salt of one or more of the compounds described herein. In such embodiments, the salt may include a counter anion. For example, the hydrate inhibitor compound may include a salt with a counter anion X. In certain embodiments, such salts may wholly or partially dissociate in aqueous solution. In other embodiments, the salts may remain substantially associated (either with the original anion or with other ions from solution). Suitable counter anions may include, for example, a carboxylate, a halide, a sulfate, a sulfonate, a hydroxide, a phosphonate, and/or any combination thereof. It will be appreciated by one of ordinary skill in the art having the benefit of this disclosure that salts may be formed with other counter anions instead of or in addition to the counter anions specifically disclosed herein.

In some embodiments the present disclosure provides methods of using the hydrate inhibitor compounds. In certain embodiments, the hydrate inhibitor compounds of the present disclosure may be used to inhibit, retard, mitigate, reduce, control, and/or delay the formation of one or more hydrates or agglomerates of hydrates. For example, the hydrate inhibitor compounds of the present disclosure may be used to reduce and/or prevent hydrate particles from agglomerating by, for example, helping the hydrate particles to remain small in size, well-dispersed in a fluid, and/or non-adherent to other hydrate particles and surfaces the hydrate particles may contact (e.g., a conduit wall).

In certain embodiments, one or more hydrate inhibitor compounds of the present disclosure may be introduced into a fluid that includes any one or more of water, a gas, a liquid hydrocarbon, and any combination thereof. Although listed separately from liquid hydrocarbons, the gas may in some embodiments include gaseous hydrocarbon, though the gas need not necessarily include hydrocarbon.

In some embodiments, the hydrate inhibitor compounds of the present disclosure initially may be incorporated into a composition prior to being introduced into the fluid to be treated. The fluid may be any suitable fluid in which the hydrate inhibitor compound may be included. For example, in some embodiments, the composition may be a treatment fluid for use in a wellbore penetrating a subterranean formation during, for instance, oil and/or gas recovery operations. The composition may include a solvent for the hydrate inhibitor compound. Suitable solvents include, for example, any alcohol, methanol, isopropyl alcohol, glycol, ethylene glycol, any organic solvent, toluene, xylene, monobutyl ether, hexane, cyclohexane, and/or any combination thereof.

In certain embodiments, the fluid into which one or more hydrate inhibitor compounds may be incorporated may optionally include any number of additives. Examples of such additives include, but are not limited to, salts, surfactants, acids, proppant particulates, diverting agents, fluid loss control additives, nitrogen, carbon dioxide, surface modifying agents, tackifying agents, foamers, corrosion inhibitors, scale inhibitors, other hydrate inhibitors, catalysts, clay control agents, biocides, friction reducers, antifoam agents, bridging agents, flocculants, $H_2S$ scavengers, $CO_2$ scavengers, oxygen scavengers, lubricants, viscosifiers, breakers, weighting agents, relative permeability modifiers, resins, wetting agents, coating enhancement agents, filter cake removal agents, antifreeze agents (e.g., ethylene glycol), and the like. A person skilled in the art, with the benefit of this disclosure, will recognize the types of additives that may be included in the fluids of the present disclosure for a particular application. It further will be appreciated by one of ordinary skill in the art having the benefit of the present disclosure that the amount of the hydrate inhibitor compounds of the present disclosure effective for inhibiting, retarding, reducing, controlling, delaying, and/or the like hydrates may depend upon, for example, the volume of water in the fluid and/or additives in the fluid.

In certain embodiments, the hydrate inhibitor compound may be introduced into the fluid to be treated through a conduit or an injection point. In certain embodiments, one or more hydrate inhibitor compounds of the present disclosure may be introduced into a wellhead, a wellbore, a subterranean formation, a conduit, a vessel, and the like, and may contact and/or be introduced into the fluid residing therein.

In certain embodiments, the fluid treated using the hydrate inhibitor compounds of the present disclosure may be flowing or it may be substantially stationary. In some instances, the fluid may be in a high-pressure, low-temperature environment such that hydrates form in the fluid. In certain embodiments, hydrates may form in the fluid when the pressure of the environment in which the fluid flows or resides is in the range from about 14.7 psi to about 20,000 psi. In certain embodiments, hydrates may form in the fluid when the temperature of the environment in which the fluid flows or resides is in the range from about 0° C. (32° F.) to about 30° C. (86° F.). In certain embodiments, the formation of hydrates in a fluid may depend on both the pressure and the temperature of the fluid and/or the environment in which the fluid is located. For example, at lower temperatures (e.g., below about 5° C. (41° F.)), methane hydrates may form over a wide range of pressures (e.g., above about 400 psi). Conversely, at higher pressures (e.g., above about 1400 psi), methane hydrates may form over a wide range of temperatures (e.g., up to about 15° C. (59° F.)).

In certain embodiments, the fluid may be within a vessel, or within a conduit (e.g., a conduit that may transport the fluid), or within a subterranean formation, or within a wellbore penetrating a portion of the subterranean formation, and/or within a wellhead of a wellbore. Examples of conduits include, but are not limited to, pipelines, production piping, subsea tubulars, process equipment, and the like as used in industrial settings and/or as used in the production of oil and/or gas from a subterranean formation, and the like. The conduit may in certain embodiments penetrate at least a portion of a subterranean formation, as in the case of an oil and/or gas well. In particular embodiments, the conduit may be a wellhead, a wellbore, or may be located within a wellbore penetrating at least a portion of a subterranean formation. Such oil and/or gas well may, for example, be a subsea well (e.g., with the subterranean formation being located below the sea floor), or it may be a surface well (e.g., with the subterranean formation being located belowground). A vessel or conduit according to other embodiments may be located in an industrial setting such as a refinery (e.g., separation vessels, dehydration units, pipelines, heat exchangers, and the like), or it may be a transportation pipeline.

In certain embodiments, one or more hydrate inhibitor compounds of the present disclosure may be introduced into and/or contact the fluid in an amount from about 0.1% to about 10% by volume based on the volume of water in the fluid (or in other words, about 0.1% to about 10% by volume based on water cut). In various embodiments, the hydrate inhibitor compounds of the present disclosure may be used as low dosage hydrate inhibitors (LDHIs) such that an effective amount of one or more hydrate inhibitor compounds for inhibiting, retarding, mitigating, reducing, controlling, delaying, and/or the like agglomeration of hydrates may be as low as any of: 0.1, 0.25, 0.50, 0.75, 1.00, 1.25, 1.50, 1.75, 2.00, 2.25, and 2.50% by volume based on water cut. An effective amount may be as high as any of: 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, and 10.0% by volume based on water cut. Thus, in some embodiments, an effective amount of hydrate inhibitor compounds of the present disclosure for inhibiting, retarding, mitigating, reducing, controlling, delaying, and/or the like agglomeration of hydrates may be about 0.1% to about 5.5% by volume based on water cut of the fluid; in other embodiments, about 0.1% to about 3.0% by volume based on water cut of the fluid; in other embodiments, about 0.25% to about 2.5% by volume based on water cut of the fluid; and in other embodiments, about 0.5% to about 2.0% by volume based on water cut of the fluid.

In certain embodiments, one or more hydrate inhibitor compounds of the present disclosure may be introduced to and/or contact any of various fluids having different water cuts (i.e., the ratio of the volume of water in the fluid to the total volume of the fluid). For example, in some embodiments the water cut of the fluid may be about 1 to about 65%. In other embodiments, the water cut may be as low as any one of: 20, 25, 30, 35, 40, 45, 50, 55, 60, and 65%; while the water cut may be as high as any one of: 35, 40, 45, 50, 55, 60, 65, 70, 75, 80, 85, 90, and 95%. In certain embodiments, a fluid may have a water cut of 30% or more, 35% or more, 40% or more, 45% or more, 50% or more, 55% or more, or 60% or more, up to about 99%. In yet other embodiments, one or more hydrate inhibitor compounds of the present disclosure may be introduced into or contact a fluid with any water cut ranging from about 0.1% to about 99%.

In certain embodiments, the hydrate inhibitor compounds of the present disclosure may be introduced into a wellhead of a wellbore penetrating at least a portion of the subterranean formation, a wellbore, a subterranean formation, a vessel, and/or a conduit—and/or into a fluid within any of the foregoing-using any method or equipment known in the art. For example, the hydrate inhibitor compounds of the present disclosure may be applied to a subterranean formation and/or wellbore using batch treatments, squeeze treatments, continuous treatments, and/or any combination thereof. In certain embodiments, a batch treatment may be performed in a subterranean formation by stopping production from the well and pumping the dissolved hydrate inhibitors into a wellbore, which may be performed at one or more points in time during the life of a well. In other embodiments, a squeeze treatment may be performed by dissolving a hydrate inhibitor compound of the present disclosure in a suitable solvent at a suitable concentration and squeezing that solvent carrying the hydrate inhibitor downhole into the formation, allowing production out of the formation to bring the hydrate inhibitor to its desired location. In other embodiments, a hydrate inhibitor compound of the present disclosure may be injected into a portion of a subterranean formation using an annular space or capillary injection system to continuously introduce the hydrate inhibitor compound into the formation. In certain embodiments, a composition (such as a treatment fluid) including a hydrate inhibitor compound of the present disclosure may be circulated in the wellbore using the same types of pumping systems and equipment at the surface that are used to introduce treatment fluids or additives into a wellbore penetrating at least a portion of the subterranean formation.

For example, a hydrate inhibitor compound of the present disclosure may be introduced into a wellbore and/or tubing using a capillary injection system as shown in FIG. 1. Referring now to FIG. 1, wellbore 105 has been drilled to penetrate a portion of a subterranean formation 100. A tubing 110 (e.g., production tubing) has been placed in the wellbore 105. A capillary injection tube 130 is disposed in the annular space between the outer surface of tubing 110 and the inner wall of wellbore 105. The capillary injection tube 130 is connected to a side-pocket mandrel 140 at a lower section of the tubing 110. A hydrate inhibitor compound of the present disclosure may be injected into capillary injection tube 130 at the wellhead 108 at the surface such that it mixes with production fluid at or near the side-pocket mandrel 140. As the production fluid flows through the tubing 110, the hydrate inhibitor compound may prevent, inhibit, retard, reduce, control, and/or delay the formation of one or more hydrates within the tubing 110. Other capillary injection systems and side pocket mandrel devices (e.g., those used in gas lift production) may be used in a similar manner to the system shown in FIG. 1.

In certain embodiments, a hydrate inhibitor compound of the present disclosure may be added to a conduit such as a pipeline where one or more fluids enter the conduit and/or at one or more other locations along the length of the conduit. In such embodiments, the hydrate inhibitor compound may be added in batches or injected substantially continuously while the pipeline is being used, for example, to maintain the concentration of the hydrate inhibitor compound of the present disclosure in the fluid at a certain amount (e.g., one or more of the concentrations referenced above).

Once introduced into a fluid, subterranean formation, wellbore, pipeline, vessel, or other location, the hydrate inhibitor compound may inhibit, retard, reduce, control, and/or delay the formation of one or more hydrates or the agglomeration of hydrate crystals within the fluid, subterranean formation, wellbore, pipeline, vessel, or other location.

To facilitate a better understanding of the present disclosure, the following examples of certain aspects of certain embodiments are given. The following examples are not the only examples that could be given according to the present disclosure and are not intended to limit the scope of the disclosure or claims.

EXAMPLE

Rocking cell tests were carried out on several samples including different hydrate inhibitor compounds having structures according to some embodiments of the present disclosure. Rocking cell tests involve the injection of oil, water, a hydrate inhibitor compound, and gas into a cell at representative conditions. Optionally, additional gas may be injected into the cell (e.g., to achieve a desired working pressure during the experiment). Each cell was of a fixed volume and maintained constant mass during the experiment; that is, oil, water, a hydrate inhibitor compound, and gas were injected at the beginning of the experiment, but thereafter the cell was closed to mass transfer in or out of the cell. Each cell also included a magnetic ball in the space where fluids are injected. The ball aided in agitation of the fluids during rocking. In addition, magnetic sensors on both ends of the cell detected whether the magnetic ball's movements through the fluids were hindered during rocking, wherein such hindrance could indicate the presence of hydrates. The cell also permitted visual observation of its contents during the experiment.

Initially, amounts of oil, water, and a hydrate inhibitor compound were injected into the cell until the desired water cut was achieved (i.e., fraction of aqueous phase by volume in the total fluid) and hydrate inhibitor compound dosage (i.e., volume % of hydrate inhibitor compound on water cut basis) of the experiment. After injection of oil, water, and hydrate inhibitor compound, gas was injected to reach a desired pressure. For example, the working pressure of a conduit of interest for evaluation of the hydrate inhibitor compound in this case was around 2,800 psi. Gas composition varied based upon the conditions that would be encountered in the target conduit for the hydrate inhibitor compound.

During the initial phase of the test, the gas inlet valves remained open while the cell was rocked for approximately 2 hours to emulsify the fluids therein and saturate the liquid phase with gas such that no further gas would be consumed by the liquid phase. During the next phase, the gas inlet valves were closed and the temperature was then ramped down from about 20° C. to about 4° C. over a period of about 1 hour. The rocking was continued for around 18 hours after the temperature reached about 4° C. The rocking was then stopped for a period of time while the cell was horizontal, simulating a system shut-in. This "shut-in" period lasted for at least 6 hours, varying only so that the re-start of rocking could be visually observed.

Visual inspection of the contents of the cell was made throughout the tests for visual ratings of the performance of the hydrate inhibitor compound as a hydrate inhibitor. Sensor data from the magnetic sensors were collected to measure performance of the hydrate inhibitor compound as a hydrate inhibitor. The performance of each LDHI was ranked as a "Pass" or "Fail" based on the visual rating and/or the sensor data. When hydrate blockages impeded the motion of the magnetic ball, the sensors and visual inspection ranked the cell as a "Fail." The particular hydrate inhibitor compound sample "Passed" when visual inspection and/or sensor data indicated no obstruction or hindrance of the magnetic ball movement during rocking. Hydrate inhibitor compounds that resulted in "Passes" were effective at preventing hydrate agglomeration.

Samples were prepared of compositions including hydrate inhibitor compounds with structures according to some embodiments of the present disclosure. The samples prepared included hydrate inhibitor compounds having the following base structure:

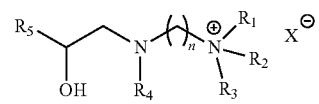

Each sample had $R_1$, $R_2$, $R_3$, $R_4$, $R_5$, $X^-$, and n as defined below in Table 1.

TABLE 1

Sample Hydrate Inhibitor Compounds

| Sample No. | $R_1$ | $R_2$ | $R_3$ | $R_4$ | $R_5$ | n | $X^-$ | Dose | Max. Water Cut to Pass Test |
|---|---|---|---|---|---|---|---|---|---|
| 1 | H | Butyl | Butyl | H | $C_{10}$ | 3 | Acetic acid | 2% | 40% |
| 2 | H | Butyl | Butyl | H | $C_{10}$ | 3 | Acrylic acid | 2% | 40% |
| 3 | Methyl | Butyl | Butyl | H | $C_{10}$ | 3 | Methyl sulfate | 2% | 40% |
| 4 | Methyl | Butyl | Butyl | H | $C_{10}$ | 3 | Methyl sulfate | 2% | 50% |
| 5 | Ethyl | Methyl | Methyl | H | $C_{10}$ | 3 | Ethyl sulfate | 2% | 40% |
| 6 | Ethyl | Methyl | Methyl | H | $C_{10}$ | 3 | Ethyl sulfate | 2% | 50% |

As also indicated in Table 1, each hydrate inhibitor compound was applied at the indicated dosage (2.0% v/v based on water cut) to fluids having various water cuts. The water in each sample had a salinity of 6% total dissolved solids. The results in Table 1 show the maximum water cut at which each sample hydrate inhibitor compound passed the rocking cell test. Thus, this example demonstrates that the compositions and methods of the present disclosure may facilitate, among other benefits, the inhibition, retardation, reduction, control, and/or delay of agglomeration of hydrates and/or hydrate-forming compounds.

An embodiment of the present disclosure is a method that includes contacting a fluid with a hydrate inhibitor composition, wherein the hydrate inhibitor composition includes at least one compound having the structural formula:

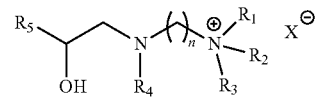

wherein $R_1$ is hydrogen or any $C_1$ to $C_8$ hydrocarbon chain, wherein each of $R_2$ and $R_3$ is independently a $C_1$ to $C_8$ hydrocarbon chain, wherein $R_4$ is hydrogen, a $C_1$ to $C_{20}$ hydrocarbon chain, or $-CH_2-CH(OH)-R_5$, wherein $R_5$ is a $C_1$ to $C_{50}$ alkyl chain or a $C_1$ to $C_{50}$ alkenyl chain, wherein $X^-$ is a counter anion, and wherein n is an integer from 1 to 8. In one or more embodiments described above, $X^-$ is selected from the group consisting of: a carboxylate, a halide, a sulfate, a sulfonate, a hydroxide, a phosphonate, and/or any combination thereof. In one or more embodiments described above, the fluid includes at least one component selected from the group consisting of: water, a gas, a liquid hydrocarbon, and any combination thereof. In one or more embodiments described above, the hydrate inhibitor composition is introduced into the fluid through a conduit or an injection point in fluid communication with a wellbore in which the fluid resides. In one or more embodiments described above, the hydrate inhibitor composition is introduced into a wellbore penetrating at least a portion of a subterranean formation through which the fluid is flowing. In one or more embodiments described above, the hydrate inhibitor composition is introduced into a conduit through which the fluid is flowing. In one or more embodiments described above, the fluid includes water and has a water cut of about 0.1% or more. In one or more embodiments described above, the fluid includes water and the hydrate inhibitor composition is provided in an amount such that the compound is present in the fluid in an amount from about 0.1% to about 10% by volume based on the water cut of the fluid. In one or more embodiments described above, $R_5$ is any $C_1$ to $C_{50}$ alkyl chain or any $C_1$ to $C_{50}$ alkenyl chain resulting from a reaction between an 1,2-epoxyalkane and a dialkylaminoalkylamine. In one or more embodiments described above, the dialkylaminoalkylamine includes one or more hetero-atoms. In one or more embodiments described above, the compound is a reaction product of a reaction between (i) an alkylating agent and (ii) a second intermediate resulting from a reaction between a dialkylaminoalkylamine and a first intermediate, wherein the first intermediate includes a 1,2-epoxyalkane.

Another embodiment of the present disclosure is a method that includes introducing a hydrate inhibitor composition into a wellbore penetrating at least a portion of a subterranean formation, wherein the hydrate inhibitor composition includes at least one compound having the structural formula:

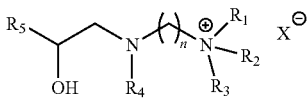

wherein $R_1$ is hydrogen or any $C_1$ to $C_8$ hydrocarbon chain, wherein each of $R_2$ and $R_3$ is independently a $C_1$ to $C_8$ hydrocarbon chain, wherein $R_4$ is hydrogen, a $C_1$ to $C_{20}$ hydrocarbon chain, or —$CH_2$—$CH(OH)$—$R_5$, and —$CH_2$—$CH(OH)$—$R_5$, wherein $R_5$ is a $C_1$ to $C_{50}$ alkyl chain or a $C_1$ to $C_{50}$ alkenyl chain, wherein $X^-$ is a counter anion, and wherein n is an integer from 1 to 8. In one or more embodiments described above, the hydrate inhibitor composition is introduced into the wellbore through a conduit or an injection point in fluid communication with the wellbore. In one or more embodiments described above, $X^-$ is selected from the group consisting of: a carboxylate, a halide, a sulfate, a sulfonate, a hydroxide, a phosphonate, and any combination thereof.

In one or more embodiments described above, the method further includes allowing the hydrate inhibitor composition to contact a fluid residing in the wellbore. In one or more embodiments described above, the fluid includes water and has a water cut of about 0.1% or more. In one or more embodiments described above, the fluid includes at least one component selected from the group consisting of: water, a gas, a liquid hydrocarbon, and any combination thereof.

Another embodiment of the present disclosure is a composition that includes a compound having the structural formula:

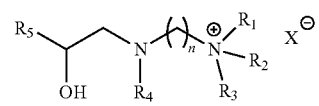

wherein $R_1$ is hydrogen or any $C_1$ to $C_8$ hydrocarbon chain, wherein each of $R_2$ and $R_3$ is independently a $C_1$ to $C_8$ hydrocarbon chain, wherein $R_4$ is hydrogen, a $C_1$ to $C_{20}$ hydrocarbon chain, or —$CH_2$—$CH(OH)$—$R_5$, wherein $R_5$ is a $C_1$ to $C_{50}$ alkyl chain or a $C_1$ to $C_{50}$ alkenyl chain, wherein $X^-$ is a counter anion, and wherein n is an integer from 1 to 8. In one or more embodiments described above, $R_5$ is any $C_1$ to $C_{50}$ alkyl chain or any $C_1$ to $C_{50}$ alkenyl chain resulting from a reaction between an 1,2-epoxyalkane and a dialkylaminoalkylamine. In one or more embodiments described above, the composition further includes a solvent selected from the group consisting of: an alcohol, methanol, isopropyl alcohol, glycol, ethylene glycol, an organic solvent, toluene, xylene, monobutyl ether, hexane, cyclohexane, and any combination thereof.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. While numerous changes may be made by those skilled in the art, such changes are encompassed within the spirit of the subject matter defined by the appended claims. Furthermore, no limitations are intended to the details of construction or design herein shown, other than as described in the claims below. It is therefore evident that the particular illustrative embodiments disclosed above may be altered or modified and all such variations are considered within the scope and spirit of the present disclosure. In particular, every range of values (e.g., "from about a to about b," or, equivalently, "from approximately a to b," or, equivalently, "from approximately a-b") disclosed herein is to be understood as referring to the power set (the set of all subsets) of the respective range of values. The terms in the claims have their plain, ordinary meaning unless otherwise explicitly and clearly defined by the patentee.

What is claimed is:
1. A method comprising:
   contacting a fluid with a hydrate inhibitor composition, wherein the hydrate inhibitor composition comprises at least one compound having the structural formula:

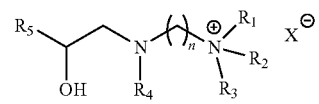

wherein $R_1$ is hydrogen or any $C_1$ to $C_8$ hydrocarbon chain, wherein each of $R_2$ and $R_3$ is independently a $C_1$ to $C_{88}$ hydrocarbon chain, wherein $R_4$ is hydrogen, a $C_1$ to $C_{20}$ hydrocarbon chain, or —$CH_2$—$CH(OH)$—$R_5$, wherein $R_5$ is a $C_1$ to $C_{50}$ alkyl chain or a $C_1$ to $C_{50}$ alkenyl chain, wherein $X^-$ is a counter anion, wherein n is an integer from 1 to 8, and wherein: (i) the hydrate inhibitor composition is introduced into the fluid through a conduit or an injection point in fluid communication with a wellbore in which the fluid resides or (ii) the hydrate inhibitor composition is introduced into a wellbore penetrating at least a portion of a subterranean formation through which the fluid is flowing.

2. The method of claim 1 wherein $X^-$ is selected from the group consisting of: a carboxylate, a halide, a sulfate, a sulfonate, a hydroxide, a phosphonate, and any combination thereof.

3. The method of claim 1 wherein the fluid comprises at least one component selected from the group consisting of: water, a gas, a liquid hydrocarbon, and any combination thereof.

4. A method comprising:
contacting a fluid with a hydrate inhibitor composition, wherein the hydrate inhibitor composition comprises at least one compound having the structural formula:

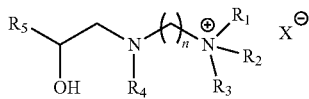

wherein $R_1$ is hydrogen or any $C_1$ to $C_8$ hydrocarbon chain, wherein each of $R_2$ and $R_3$ is independently a $C_1$ to $C_8$ hydrocarbon chain, wherein $R_4$ is hydrogen, a $C_1$ to $C_{20}$ hydrocarbon chain, or —$CH_2$—$CH(OH)$—$R_5$, wherein $R_5$ is a $C_1$ to $C_{50}$ alkyl chain or a $C_1$ to $C_{50}$ alkenyl chain, wherein $X^-$ is a counter anion, wherein n is an integer from 1 to 8, and wherein the hydrate inhibitor composition is introduced into a conduit through which the fluid is flowing.

5. The method of claim 1 wherein the fluid comprises water and has a water cut of about 0.1% or more.

6. The method of claim 1 wherein the fluid comprises water and the hydrate inhibitor composition is provided in an amount such that the compound is present in the fluid in an amount from about 0.1% to about 10% by volume based on the water cut of the fluid.

7. The method of claim 1 wherein $R_5$ is any $C_1$ to $C_{50}$ alkyl chain resulting from a reaction between an 1,2-epoxyalkane and a dialkylaminoalkylamine.

8. The method of claim 7, wherein the dialkylaminoalkylamine comprises one or more hetero-atoms.

9. The method of claim 1 wherein the compound is a reaction product of a reaction between (i) an alkylating agent and (ii) a second intermediate resulting from a reaction between a dialkylaminoalkylamine and a first intermediate, wherein the first intermediate comprises a 1,2-epoxyalkane.

10. A method comprising:
introducing a hydrate inhibitor composition into a wellbore penetrating at least a portion of a subterranean formation, wherein the hydrate inhibitor composition comprises at least one compound having the structural formula:

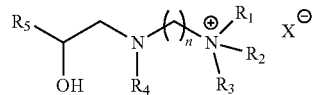

wherein $R_1$ is hydrogen or any $C_1$ to $C_8$ hydrocarbon chain, wherein each of $R_2$ and $R_3$ is independently a $C_1$ to $C_8$ hydrocarbon chain, wherein $R_4$ is hydrogen, a $C_1$ to $C_{20}$ hydrocarbon chain, or —$CH_2$—$CH(OH)$—$R_5$, wherein $R_5$ is a $C_1$ to $C_{50}$ alkyl chain or a $C_1$ to $C_{50}$ alkenyl chain, wherein $X^-$ is a counter anion, and wherein n is an integer from 1 to 8.

11. The method of claim 10 wherein the hydrate inhibitor composition is introduced into the wellbore through a conduit or an injection point in fluid communication with the wellbore.

12. The method of claim 10 wherein $X^-$ is selected from the group consisting of: a carboxylate, a halide, a sulfate, a sulfonate, a hydroxide, a phosphonate, and any combination thereof.

13. The method of claim 10 further comprising allowing the hydrate inhibitor composition to contact a fluid residing in the wellbore.

14. The method of claim 13 wherein the fluid comprises water and has a water cut of about 0.1% or more.

15. The method of claim 13 wherein the fluid comprises at least one component selected from the group consisting of: water, a gas, a liquid hydrocarbon, and any combination thereof.

16. A method comprising:
contacting a fluid with a hydrate inhibitor composition, wherein the hydrate inhibitor composition comprises at least one compound having the structural formula:

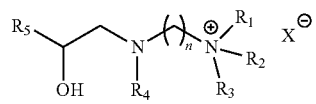

wherein $R_1$ is hydrogen or any $C_1$ to $C_8$ hydrocarbon chain, wherein each of $R_2$ and $R_3$ is independently a $C_1$ to $C_8$ hydrocarbon chain, wherein $R_4$ is hydrogen, a $C_1$ to $C_{20}$ hydrocarbon chain, or —$CH_2$—$CH(OH)$—$R_5$, wherein $R_5$ is a $C_1$ to $C_{50}$ alkyl chain or a $C_1$ to $C_{50}$ alkenyl chain, wherein $X^-$ is a counter anion, wherein n is an integer from 1 to 8, and wherein the fluid comprises water and (i) has a water cut of about 0.1% or more or (ii) the hydrate inhibitor composition is provided in an amount such that the compound is present in the fluid in an amount from about 0.1% to about 10% by volume based on the water cut of the fluid.

17. The method of claim 16 wherein $X^-$ is selected from the group consisting of: a carboxylate, a halide, a sulfate, a sulfonate, a hydroxide, a phosphonate, and any combination thereof.

18. The method of claim 10 wherein $R_5$ is any $C_1$ to $C_{50}$ alkyl chain resulting from a reaction between an 1,2-epoxyalkane and a dialkylaminoalkylamine.

19. The method of claim 18, wherein the dialkylaminoalkylamine comprises one or more hetero-atoms.

20. The method of claim 10 wherein the compound is a reaction product of a reaction between (i) an alkylating agent and (ii) a second intermediate resulting from a reaction between a dialkylaminoalkylamine and a first intermediate, wherein the first intermediate comprises a 1,2-epoxyalkane.

* * * * *